United States Patent
Ishii et al.

(10) Patent No.: US 11,158,819 B2
(45) Date of Patent: Oct. 26, 2021

(54) P-TYPE ORGANIC SEMICONDUCTOR, COMPOSITION, PHOTOELECTRIC CONVERSION FILM, PHOTOELECTRIC CONVERSION DEVICE, AND IMAGE SENSOR

(71) Applicant: Samsung Electronics Co., Ltd., Suwon-si (KR)

(72) Inventors: Norihito Ishii, Suwon-si (KR); Katsunori Shibata, Hwaseong-si (KR); Naotoshi Suganuma, Yokohama (JP)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 16/726,416

(22) Filed: Dec. 24, 2019

(65) Prior Publication Data

US 2020/0212317 A1   Jul. 2, 2020

(30) Foreign Application Priority Data

Dec. 27, 2018 (JP) .............................. JP2018-245279
Dec. 23, 2019 (KR) ......................... 10-2019-0172872

(51) Int. Cl.
  *C07D 487/22* (2006.01)
  *H01L 51/00* (2006.01)
  *H01L 27/30* (2006.01)
  *C07F 7/22* (2006.01)

(52) U.S. Cl.
  CPC ........ *H01L 51/0077* (2013.01); *C07D 487/22* (2013.01); *C07F 7/2284* (2013.01); *H01L 27/307* (2013.01)

(58) Field of Classification Search
  CPC .................................................. C07D 487/22
  See application file for complete search history.

(56) References Cited

U.S. PATENT DOCUMENTS

| | | | |
|---|---|---|---|
| 10,276,818 B2 | 4/2019 | Tamaki | |
| 10,317,287 B2 | 6/2019 | Shimasaki et al. | |
| 2018/0219047 A1 | 8/2018 | Tokuhara et al. | |
| 2019/0214590 A1 | 7/2019 | Tamaki | |

FOREIGN PATENT DOCUMENTS

| JP | 02004865 | * | 1/1990 |
|---|---|---|---|
| JP | 1998036830 | | 2/1998 |
| JP | 2009218369 A | | 9/2009 |
| JP | 2011155185 A | | 8/2011 |
| JP | 2016225456 A | | 12/2016 |
| JP | 2017183747 A | | 10/2017 |

* cited by examiner

*Primary Examiner* — Brian E McDowell
(74) *Attorney, Agent, or Firm* — Harness, Dickey & Pierce, P.L.C.

(57) ABSTRACT

Provided are a p-type organic semiconductor represented by Chemical Formula (1), which has improved thermal resistance and may detect near-infrared light, and a photoelectric conversion film, a photoelectric conversion device, and an image sensor including the same:

Chemical Formula (1)

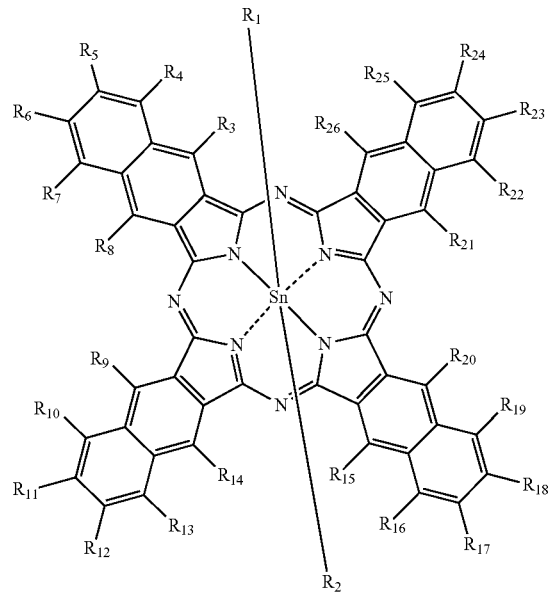

(1)

In Chemical Formula (1), $R_1$ and $R_2$ are independently a substituted or unsubstituted C1 to C30 alkyl group, and $R_3$ to $R_{26}$ are independently a hydrogen atom, a deuterium atom, a substituted or unsubstituted alkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, an oxy group substituted with a substituted or unsubstituted heterocyclic group, a thio group substituted with a substituted or unsubstituted heterocyclic group, or a substituted or unsubstituted amino group.

18 Claims, 6 Drawing Sheets

P-TYPE ORGANIC SEMICONDUCTOR, COMPOSITION, PHOTOELECTRIC CONVERSION FILM, PHOTOELECTRIC CONVERSION DEVICE, AND IMAGE SENSOR

CROSS-REFERENCE TO RELATED APPLICATION

This application claims priority to and the benefit of Japanese Patent Application No. 2018-245279, filed in the Japanese Patent Office on Dec. 27, 2018, and of Korean Patent Application No. 10-2019-0172872, filed in the Korean Intellectual Property Office on Dec. 23, 2019, the entire contents of which are incorporated herein by reference.

BACKGROUND

1. Field

A p-type organic semiconductor, a composition, a photoelectric conversion film, a photoelectric conversion device, and an image sensor are disclosed.

2. Description of Related Art

Organic semiconductors may easily change their characteristics by changing molecular structures, so that they may be applied and varied in various applications. Therefore, organic semiconductors have been actively researched because they are thought to realize functions that cannot be realized in inorganic semiconductors.

Recently, development of an image sensor capable of simultaneously acquiring an image by visible light and an image by near-infrared light is in progress. Such an image sensor has a photoelectric conversion device (light receiving device) in which a photoelectric conversion film including a semiconductor capable of detecting near-infrared light is formed between a pair of electrodes.

Herein, in the case of inorganic semiconductors, it is difficult to design a device to absorb only near-infrared light. On the other hand, since organic semiconductors may be designed to absorb near-infrared light alone, organic semiconductors are used in photoelectric conversion films capable of detecting near-infrared light.

For example, Patent Reference 1 discloses a derivative of tin naphthalocyanine as a p-type organic semiconductor included in a photoelectric conversion film capable of detecting near-infrared light.

PRIOR ART DOCUMENTS

Patent Reference

Japanese Patent Laid-Open Publication No. 2016-225456

SUMMARY

Although the photoelectric conversion film including the p-type organic semiconductor of Patent Reference 1 may be formed by a resistive heating degradation deposition method, the p-type organic semiconductor is thermally degraded, and as a result, conversion efficiency of a photoelectric conversion device may be deteriorated.

Therefore, there are needs for a p-type organic semiconductor that has improved heat resistance and capable of detecting near-infrared light.

An embodiment provides a p-type organic semiconductor represented by Chemical Formula (1):

Chemical Formula (1)

(1)

In Chemical Formula (1), $R_1$ and $R_2$ are independently a substituted or unsubstituted C1 to C30 alkyl group, and $R_3$ to $R_{26}$ are independently a hydrogen atom, a deuterium atom, a substituted or unsubstituted alkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, an oxy group substituted with a substituted or unsubstituted heterocyclic group, a thio group substituted with a substituted or unsubstituted heterocyclic group, or a substituted or unsubstituted amino group.

Another embodiment provides a composition including a p-type organic semiconductor according to an embodiment and an n-type organic semiconductor.

Another embodiment provides a photoelectric conversion film manufactured by using the composition according to the embodiment.

Another embodiment provides a photoelectric conversion device including a photoelectric conversion film according to an embodiment.

Another embodiment provides an image sensor including a photoelectric conversion device according to an embodiment.

According to an embodiment, it is possible to provide a p-type organic semiconductor having improved heat resistance and capable of detecting near-infrared light. A photoelectric conversion film and a photoelectric conversion device which are capable of detecting near-infrared light from a composition including such a p-type organic semiconductor and an n-type organic semiconductor may be manufactured. Such a photoelectric conversion device may be applied to solar cells, photosensors, photodiodes, and the like.

DETAILED DESCRIPTION

Hereinafter, embodiments of the present disclosure are described in detail.

Hereinafter, in drawings, in order to clearly express a plurality of layers and regions, the thickness is enlarged. In addition, in drawings, in order to demonstrate these embodiments clearly, parts which are unnecessary for description are omitted. In addition, throughout the specification, the same symbols are used for the same or similar constituent elements.

If a part of layers, films, areas, plates, and the like is said to be "on top" of another part, the part may be "directly on" another part and another part may exist between a part and another part. On the contrary, when a part is "directly on" another part, it means that there is no other part between one part and another part.

The p-type organic semiconductor according to an embodiment is represented by Chemical Formula (1):

Chemical Formula (1)

In Chemical Formula (1), $R_1$ and $R_2$ are independently a substituted or unsubstituted C1 to C30 alkyl group, and $R_3$ to $R_{26}$ are independently a hydrogen atom, a deuterium atom, a substituted or unsubstituted alkyl group, a substituted or unsubstituted aryl group, a substituted or unsubstituted alkoxy group, a substituted or unsubstituted alkylthio group, a substituted or unsubstituted aryloxy group, a substituted or unsubstituted arylthio group, an oxy group substituted with a substituted or unsubstituted heterocyclic group, a thio group substituted with a substituted or unsubstituted heterocyclic group, or a substituted or unsubstituted amino group.

Since the p-type organic semiconductor according to an embodiment is a derivative of tin naphthalocyanine, it may detect near-infrared light.

In addition, the p-type organic semiconductor according to an embodiment has improved heat resistance because it has $R_1$ and $R_2$ as axial substituents of tin naphthalocyanine derivatives. Therefore, when the photoelectric conversion film including the p-type organic semiconductor according to an embodiment is formed by a resistive heating deposition method, thermal degradation of the p-type organic semiconductor may be reduced and/or suppressed, and as a result, conversion efficiency of a photoelectric conversion device described below may be improved.

The alkyl group of $R_3$ to $R_{26}$ in Chemical Formula (1) may be a linear, branched, or cyclic alkyl group.

The linear alkyl group may include, for example, a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, and the like, but is not limited thereto. For example, the linear alkyl group may be a methyl group, an ethyl group, a propyl group, a butyl group, an octyl group, a decyl group, a pentadecyl group, and the like.

Examples of the branched alkyl group may include, but are not limited to, for example, an isopropyl group, an isobutyl group, a tert-butyl group, and the like.

Examples of the cyclic alkyl group include, but are not limited to, for example, a cyclopropyl group, a cyclobutyl group, a cyclopentyl group, a cyclohexyl group, a cycloheptyl group, a cyclooctyl group, a cyclononyl group, a cyclodecyl group, and the like. For example, the cyclic alkyl group may be a cyclobutyl group, a cyclopentyl group, a cyclohexyl group, a cycloheptyl group, and the like.

The carbon number of the linear or branched alkyl group may be 1 to 30, for example, 1 to 20, for example, 1 to 18, 1 to 16, 1 to 14, 1 to 12, 1 to 10, 1 to 8, 1 to 7, 1 to 6, 1 to 5, 1 to 4, or 1 to 3, but is not limited thereto.

The carbon number of the cyclic alkyl group may be 3 to 30, for example, 3 to 20, 3 to 18, 3 to 16, 3 to 14, 3 to 12, 3 to 10, 3 to 8, or 3 to 6, but is not limited thereto.

The aryl group of $R_3$ to $R_{26}$ in Chemical Formula (1) may be a monocyclic, non-condensed polycyclic, or condensed polycyclic aryl group.

Examples of the monocyclic aryl group include, but are not limited to, for example a phenyl group.

Examples of the non-condensed polycyclic aryl group include, but are not limited to, for example, a biphenyl group, a terphenyl group, a quaterphenyl group, a quinquephenyl group, and a ceciphenyl group.

The condensed polycyclic aryl group may include, for example, a naphthyl group, an anthryl group, a phenanthryl group, a triphenylenyl group, a fluorenyl group, a fluoranthenyl group, an indenyl group, a pyrenyl group, an acetonaphtenyl group, a bisphenylfluorenyl group, a 9-(9-fluorenyl) fluorenyl group, and the like.

The ring-forming carbon number of the aryl group of the monocyclic, non-condensed polycyclic, or condensed polycyclic may be 6 to 50, for example, 6 to 40, 6 to 30, 6 to 20, 6 to 18, 6 to 14, or 6 to 10, but is not limited thereto.

The alkyl group in the alkoxy group or the alkylthio group of $R_3$ to $R_{26}$ in Chemical Formula (1) is the same as the aforementioned alkyl group.

The aryl group in the aryloxy group or the arylthio group of $R_3$ to $R_{26}$ in Chemical Formula (1) is the same as the aforementioned aryl group.

The heterocyclic group in the oxy group substituted with the heterocyclic group or the thio group substituted or unsubstituted with the heterocyclic group of $R_3$ to $R_{26}$ in Chemical Formula (1) is a monocyclic or polycyclic heterocyclic group.

The monocyclic heterocyclic group may include, for example, a pyrrolyl group, an imidazolyl group, a pyrazolyl group, an oxazolyl group, an isoxazolyl group, an oxadiazolyl group, a thiazolyl group, a furanyl group, a pyranyl group, a thienyl group, a pyridyl group, a pyrazyl group, a pyrimidinyl group, a pyridazinyl group, a triazinyl group, a quinolyl group, an isoquinolyl group, and the like, but is not limited to thereto.

The polycyclic heterocyclic group may include, for example, a benzo (pyridyl) furanyl group, a benzofuranyl group, a benzothienyl group, an indryl group, a carbazolyl group, a carbolinyl group, a phenantridinyl group, an acridinyl group, a perimidinyl group, a phenanthrolinyl group, a benzooxazolyl group, a benzothiazolyl group, a quinoxalyl group, a benzoimidazolyl group, a pyrazolyl group, a dibenzofuranyl group, a dibenzothienyl group, and the like, but is not limited to thereto.

The ring-forming carbon number of the monocyclic or polycyclic heterocyclic group may be 4 to 50, for example, 4 to 40, 4 to 30, 4 to 20, 5 to 50, 5 to 40, 5 to 30, 5 to 20, 5 to 15, or 5 to 10, but is not limited thereto.

In an example embodiment, $R_1$ and $R_2$ of Chemical Formula (1) may independently be a substituted or unsubstituted C3 to C20 branched alkyl group.

In an example embodiment, $R_3$ to $R_{26}$ of Chemical Formula (1) may independently be a hydrogen atom, a deuterium atom, a substituted or unsubstituted C1 to C10 alkyl group, a substituted or unsubstituted C6 to C20 aryl group, a substituted or unsubstituted C1 to C10 alkoxy group, a substituted or unsubstituted C1 to C10 alkylthio group, a substituted or unsubstituted C6 to C10 aryloxy group, a substituted or unsubstituted C6 to C10 arylthio group, an oxy group substituted with a substituted or unsubstituted C4 to C10 heterocyclic group, a thio group substituted with a substituted or unsubstituted C4 to C10 heterocyclic group, or a substituted or unsubstituted C1 to C10 amino group.

In an example embodiment, $R_3$ to $R_{26}$ may independently be a hydrogen atom or a deuterium atom. In this case, the thermal resistance of the p-type organic semiconductor may further be improved.

The substituent in $R_1$ to $R_{26}$ of Chemical Formula (1) may be, for example a cyano group, a silyl group, a C1 to C10 monoalkylsilyl group, a dialkylsilyl group or trialkylsilyl group, a C1 to C10 linear, branched or cyclic alkyl group, a C1 to C10 linear or branched alkoxy group, a ring-forming C6 to C15 aryl group, a ring-forming C6 to C15 aryloxy group, a ring-forming C6 to C15 arylcarbonyl group, a ring-forming C3 to C32 heterocyclic group, a C1 to C10 monoalkylamino group or dialkylamino group, a ring-forming C6 to C15 monoarylamino group or diarylamino group, and the like, but is not limited thereto.

On the other hand, in Chemical Formula (1), when $R_3$ to $R_{26}$ is an electron withdrawing group such as, a halogen atom, for example, F, Cl, and the like, it becomes an n-type organic semiconductor (see for example, Japanese Patent Laid-Open Publication No. 2009-218369).

The p-type organic semiconductor according to an embodiment may be represented by Chemical Formula (2):

Chemical Formula (2)

(2)

In Chemical Formula (2), $n_1$ and $n_2$ are independently an integer of 0 to 10, $Y_1$ to $Y_6$ are independently a linear alkyl group, $R_3$ to $R_{26}$ are independently the same as defined in Chemical Formula (1), and $R_{27}$ to $R_{30}$ are independently a hydrogen atom or a deuterium atom.

In Chemical Formula (2), $Y_1$ to $Y_6$ may independently be a linear C1 to C27 alkyl group, wherein a sum of the $n_1$ value and the carbon number of $Y_1$ to $Y_3$ may be 3 to 29, and a sum of the $n_2$ value and the carbon number of $Y_4$ to $Y_6$ may be 3 to 29. The carbon number of a linear alkyl group of each $Y_1$ to $Y_6$ of Chemical Formula (2) may vary depending on the values of $n_1$ and $n_2$ of Chemical Formula (2). That is, since each of $R_1$ and $R_2$ independently represents a C1 to C30 alkyl group, the sum of the $n_1$ value of the Chemical Formula (2) and the carbon number of the linear alkyl group of $Y_1$ to $Y_3$ may be 3 to 29. In addition, the sum of the $n_2$ value of Chemical Formula (2) and the carbon number of the linear alkyl group of $Y_4$ to $Y_6$ may also be 3 to 29. For example, when $n_1$ and $n_2$ of Chemical Formula (2) are independently 1, the sum of the carbon numbers of the linear alkyl groups of $Y_1$ to $Y_3$ may be 3 to 28, and the sum of the carbon numbers of linear alkyl groups of $Y_4$ to $Y_6$ may also be 3 to 28. For example, when $n_1$ and $n_2$ in Chemical Formula (2) are both 2, a sum of the carbon numbers of linear alkyl groups of each $Y_1$ to $Y_3$ may be 3 to 27, and the sum of the carbon numbers of linear alkyl groups of each $Y_4$ to $Y_6$ may also be 3 to 27.

In an example embodiment, $n_1$ and $n_2$ of Chemical Formula (2) may be all 0, and $Y_1$ to $Y_6$ may be all methyl groups.

$R_3$ to $R_{26}$ of Chemical Formula (2) may independently be a hydrogen atom, a deuterium atom, a substituted or unsubstituted C1 to C10 alkyl group, a substituted or unsubstituted C6 to C20 aryl group, a substituted or unsubstituted C1 to C10 alkoxy group, a substituted or unsubstituted C1 to C10 alkylthio group, a substituted or unsubstituted C6 to C10 aryloxy group, a substituted or unsubstituted C6 to C10 arylthio group, an oxy group substituted with a substituted or unsubstituted C4 to C10 heterocyclic group, a thio group substituted with a substituted or unsubstituted C4 to C10 heterocyclic group, or a substituted or unsubstituted C1 to C10 amino group.

In an example embodiment, $R_3$ to $R_{26}$ of Chemical Formula (2) may independently be a hydrogen atom or a deuterium atom.

When the p-type organic semiconductor according to an embodiment is represented by Chemical Formula (2), heat resistance of the p-type organic semiconductor may further be improved.

In an example embodiment, $n_1$ and $n_2$ of Chemical Formula (2) are all 0, $Y_1$ to $Y_6$ may be all methyl groups, $R_3$ to $R_{26}$ may independently be a hydrogen atom or a deuterium atom.

Another embodiment provides a composition including a p-type organic semiconductor according to an embodiment and an n-type organic semiconductor. The composition according to an embodiment may be used to form a photoelectric conversion film.

The n-type organic semiconductor may be any one as long as it forms a pn junction with the p-type organic semiconductor according to an embodiment, and is not particularly limited, but for example, sub-phthalocyanine, fullerene and a derivative thereof, or thiophene and a derivative thereof, and it may be used alone or in combination of two or more.

Among them, fullerene and/or the derivative thereof may be included in view of the conversion efficiency of the photoelectric conversion film.

Examples of the fullerene include, for example, C50, C60, C70, C76, C78, C80, C82, C84, C90, C96, C240, C540, and the like.

The derivative of the fullerene include fullerene which is substituted by a substituent.

Examples of the substituent may include, for example, the aforementioned alkyl group, aryl group, heterocyclic group, and the like, but are not limited thereto.

Figure 1:
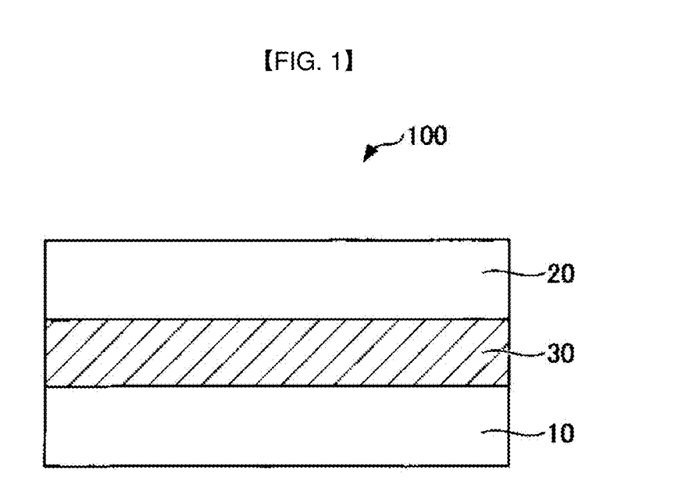
FIG. 1 is a schematic cross-sectional view showing an example of a photoelectric conversion device according to an embodiment.

FIG. 1 shows an example of a photoelectric conversion device according to an embodiment.

A photoelectric conversion device 100 includes a (organic) photoelectric conversion film 30 formed between a first electrode 10 and a second electrode 20.

At least one of the first electrode 10 and the second electrode 20 is a light-transmitting electrode that may transmit near-infrared light.

Examples of the material constituting the light-transmitting electrode include, for example, a conductive material such as indium tin oxide (ITO), indium zinc oxide (IZO), AZO, FTO, $SnO_2$, $TiO_2$, $ZnO_2$, and the like.

The light-transmitting electrode may be formed as a single layer or a plurality of layers stacked.

When the first electrode 10 or the second electrode 20 is a non-light-transmitting electrode that does not transmit near-infrared light, a material constituting the non-light-transmitting electrode may include, for example a metal such as aluminum (Al), copper, gold, silver, and the like, or polysilicon that is doped with impurities to have conductivity, and the like.

When forming the first electrode 10 and the second electrode 20, various methods may be applied depending on the used material.

For example, when an ITO electrode is formed, an electron beam method, a sputtering method, a resistive thermal deposition method, a chemical reaction method (sol-gel method, etc.), a method of coating dispersion of indium tin oxide, and the like may be used.

In addition, when the first electrode 10 and the second electrode 20 are formed, UV-ozone treatment, plasma treatment, or the like may be performed.

Herein, the first electrode 10 may be an electrode collecting holes of charges generated in the photoelectric conversion film 30. In addition, the second electrode 20 may be an electrode collecting electrons of charges generated in the photoelectric conversion film 30.

By applying a bias voltage between the first electrode 10 and the second electrode 20, it is possible to transfer holes of charges generated in the photoelectric conversion film 30 to the first electrode 10, and to transfer the electrons to the second electrode 20.

Here, when the photoelectric conversion device 100 is applied to an image sensor which is described below, converted voltage signals may be read according to amounts of holes transferred to the first electrode 10. Thereby, near-infrared light may be converted into a voltage signal and taken out.

In addition, a bias voltage may be applied to collect electrons from the first electrode 10 and to collect holes from the second electrode 20.

The photoelectric conversion film 30 includes a p-type organic semiconductor according to an embodiment and an n-type organic semiconductor, and the p-type organic semiconductor according to an embodiment and the n-type organic semiconductor form a pn junction. The photoelectric conversion film 30 generates excitons when receiving near-infrared light. After the excitons are separated into holes and electrons, the holes are transferred to the first electrode 10, and the electrons are transferred to the second electrode 20, whereby, current flows in the photoelectric conversion device 100.

The n-type organic semiconductor may be the same as the n-type organic semiconductor included in the composition according to an embodiment.

The photoelectric conversion film 30 may be formed in a single layer, or a plurality of layers stacked.

The photoelectric conversion film 30 formed of a single layer may be an intrinsic semiconductor layer.

A stack structure of the photoelectric conversion film 30 in which a plurality of layers are stacked may include, for example, a p-type semiconductor layer/intrinsic semiconductor layer, an intrinsic semiconductor layer/n-type semiconductor layer, a p-type semiconductor layer/intrinsic semiconductor layer/n-type semiconductor layer, a p-type semiconductor layer/n-type semiconductor layer, and the like.

The intrinsic semiconductor layer may include a p-type organic semiconductor according to an embodiment, and an n-type organic semiconductor.

A volume ratio of the n-type organic semiconductor to the p-type organic semiconductor according to an embodiment in the intrinsic semiconductor layer may be about 0.01 to about 100, for example, about 0.02 to about 95, about 0.02 to about 90, or about 0.05 to about 90. Thereby, the conversion efficiency of the photoelectric conversion film 30 may further be improved.

The p-type semiconductor layer includes the p-type organic semiconductor according to an embodiment.

The n-type semiconductor layer includes an n-type organic semiconductor.

A thickness of the photoelectric conversion film 30 may be about 1 nm to about 800 nm, for example, about 5 nm to about 500 nm, about 5 nm to about 400 nm, about 5 nm to about 350 nm, about 5 nm to about 300 nm, about 5 nm to about 250 nm, about 5 nm to about 200 nm, about 5 nm to about 150 nm, about 5 nm to about 100 nm, about 10 nm to about 500 nm, about 10 nm to about 400 nm, about 10 nm to about 300 nm, about 10 nm to about 200 nm, and the like, but is not limited thereto. By adjusting the thickness of the photoelectric conversion film 30 within the ranges, the conversion efficiency of the photoelectric conversion film 30 may further be improved.

The photoelectric conversion film 30 may be formed by a dry film-forming method, a resistive thermal deposition method, but may also be formed by a wet film forming method.

The dry film-forming method may include, for example, a vacuum deposition method.

Specific examples of the vacuum deposition method may include an electron beam method, a sputtering method, a resistive thermal deposition method, and the like, but are not limited thereto.

The wet film-forming method may include, for example, a solution coating method.

Specific examples of the solution coating method may include a casting method, a spin coating method, a dip coating method, a blade coating method, a wire bar coating method, a spray coating method, an inkjet printing method, a screen printing method, an offset printing method, an iron plate printing method, or the like, but is not limited thereto.

Specific examples of patterning methods when patterning of the photoelectric conversion film 30 is required (or done) may include, but are not limited to, a resist etching method, a laser removal method, or the like.

Figure 2:
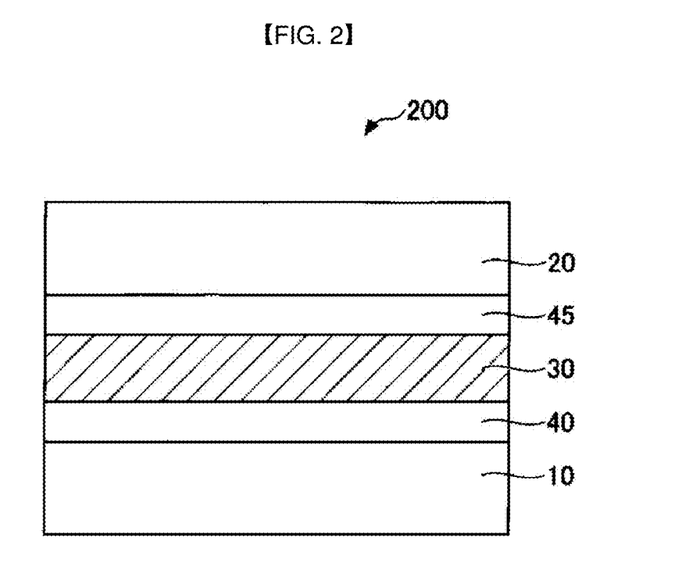
FIG. 2 is a schematic cross-sectional view showing another example of a photoelectric conversion device according to an embodiment.

FIG. 2 shows another example of a photoelectric conversion device according to an embodiment.

A photoelectric conversion device 200 is the same as the photoelectric conversion device 100, except that an electron blocking layer 40 and a hole blocking layer 45 are further formed between the first electrode 10 and the photoelectric conversion film 30 and the second electrode 20 and the photoelectric conversion film 30, respectively.

The electron blocking layer 40 limits and/or suppresses injection of electrons into the photoelectric conversion film 30 from the first electrode 10, and also limits and/or suppresses the movement of electrons generated from the photoelectric conversion film 30 to the first electrode 10.

The hole blocking layer 45 limits and/or suppresses the injection of holes into the photoelectric conversion film 30 from the second electrode 20, and also limits and/or suppresses the movement of the holes generated in the photoelectric conversion film 30 to the second electrode 20.

Examples of the material constituting the electron blocking layer 40 may include poly(3,4-ethylenedioxythiophene):poly(styrenesulfonate) (PEDOT: PSS), polyarylamine, poly(N-vinylcarbazole), polyaniline, polypyrrole, N,N,N', N'-tetrakis(4-methoxyphenyl) benzidine (TPD), 4,4'-bis[N-(1-naphthyl)-N-phenyl-amino] biphenyl (α-NPD), m-MTDATA, 4,4',4''-tris(N-carbazoleyl) triphenylamine (TCTA), and the like, and are not limited thereto. These materials may be used alone or in a combination of two or more types.

Examples of the material constituting the hole blocking layer 45 may include for example naphthalene-1,4,5,8-tetracarbonic acid dianhydride (NTCDA), bathocuproine (BCP), LiF, Alq3, Gaq3, Inq3, Znq2, Zn(BTZ)(2), BeBq2, and the like, but are not limited to these materials. These materials may be used alone or in a combination of two or more types.

Meanwhile, one or more of the electron blocking layer 40 or the hole blocking layer 45 may be omitted.

In addition, a bias voltage may be applied so as to collect electrons from the first electrode 10 and to collect holes from the second electrode 20. In this case, instead of the electron blocking layer 40 and the hole blocking layer 45, the hole blocking layer 40 and the electron blocking layer 45 may be formed, respectively.

The photoelectric conversion device according to an embodiment may be applied to an image sensor, a solar cell, a photodetector, a photosensor, a photodiode, and the like.

Figure 3:
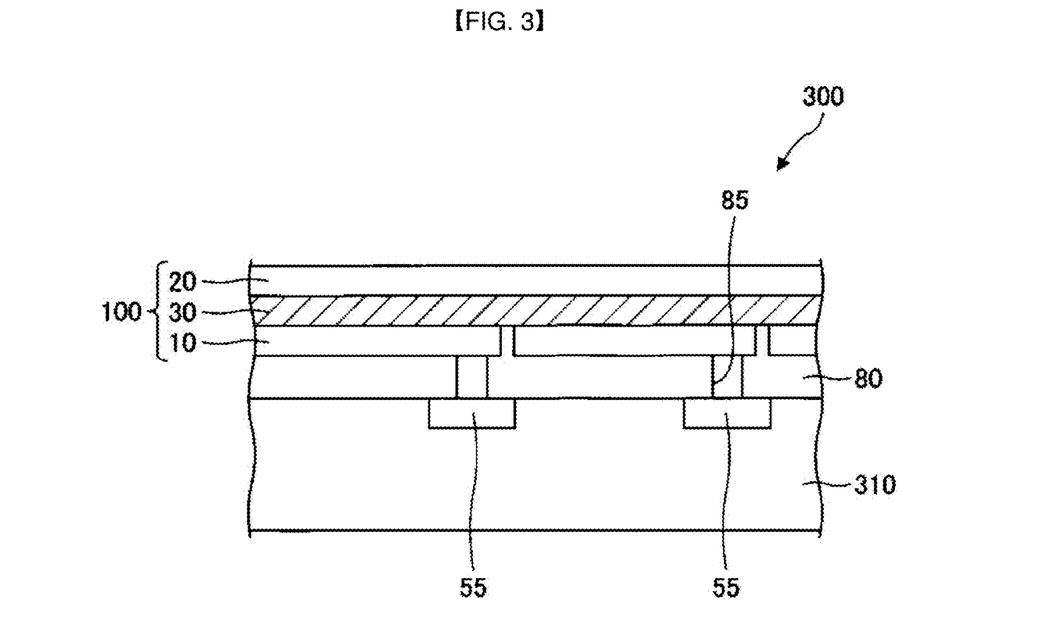
FIG. 3 is a schematic cross-sectional view showing a first example of an image sensor according to an embodiment.

FIG. 3 shows one example of an image sensor according to an embodiment.

The image sensor 300 includes a semiconductor substrate 310, an insulation layer 80, and a photoelectric conversion device 100.

The semiconductor substrate 310 may be a silicon substrate in which a transmission transistor and a charge storage 55 are integrated. Herein, the transmission transistor and the charge storage 55 are integrated per pixel, the charge storage 55 is electrically connected to the photoelectric conversion device 100, and the information of the charge storage 55 is transmitted by the transmission transistor.

Metal wires and pads are provided on the semiconductor substrate 310.

Materials of the metal wires and pads are not particularly limited if they reduce delay of the signals, but may include, for example, a metal having low resistivity, such as, aluminum (Al), copper (Cu), silver (Ag), an alloy thereof, and the like.

An insulation layer 80 is formed on the semiconductor substrate 310 on which the metal wires and pads are formed.

The material constituting the insulation layer 80 may include an inorganic insulating material such as silicon oxide, silicon nitride, and the like, a material having a low dielectric constant (low-k material), such as, SiC, SiCOH, SiCO, SiOF, and the like.

The insulation layer 80 is formed with contact holes for exposing the pad and a through-hole 85 for exposing the charge storage 55 of each pixel.

The photoelectric conversion device 100 is formed on the insulation layer 80.

The photoelectric conversion device 100 includes the first electrode 10, the photoelectric conversion film 30, and the second electrode 20, and the second electrode 20 is a light-transmitting electrode capable of transmitting near-infrared light. Therefore, when light including near-infrared light is incident from the second electrode 20 side, near-infrared light is absorbed in the photoelectric conversion film 30 to be photo-electrically converted.

A band pass filter may be installed in the upper surface of the photoelectric conversion device 100 that transmits near-infrared light alone.

Figure 4:
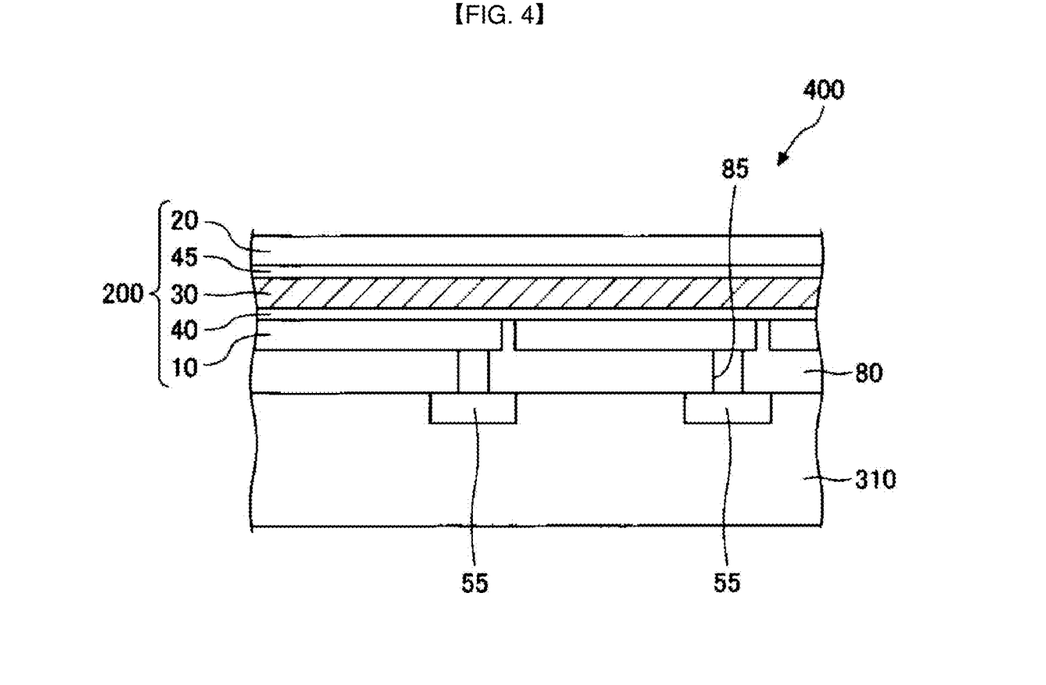
FIG. 4 is a schematic cross-sectional view showing a second example of an image sensor according to an embodiment.

FIG. 4 shows a second example of an image sensor according to an embodiment.

An image sensor 400 has the same configuration as the image sensor 300 except that the photoelectric conversion device 200 is applied instead of the photoelectric conversion device 100.

Figure 5:
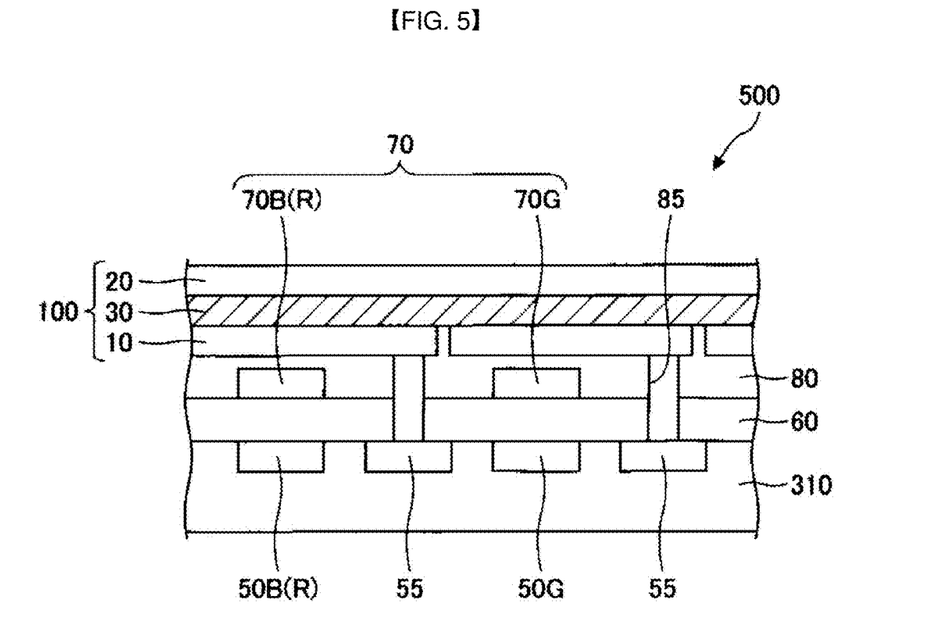
FIG. 5 is a schematic cross-sectional view showing a third example of an image sensor according to an embodiment.
Figure 6:
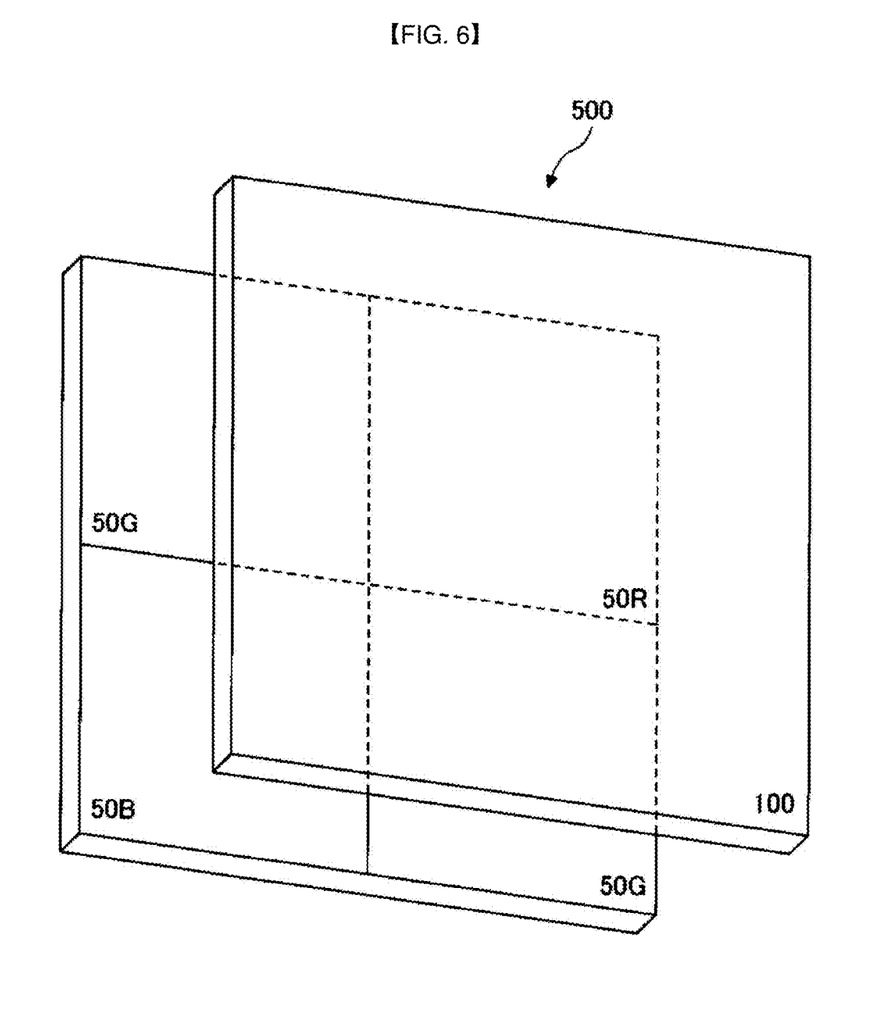
FIG. 6 is a schematic perspective view showing a third example of an image sensor according to an embodiment.

FIGS. 5 and 6 show a third example of the image sensor according to an embodiment is presented.

An image sensor 500 includes a semiconductor substrate 310, a lower insulation layer 60, a color filter layer 70, an upper insulation layer 80, and a photoelectric conversion device 100.

The semiconductor substrate 310 is a silicon substrate in which photosensitive devices 50G, 50B, and 50R, a transmission transistor, and a charge storage 55 are integrated. Here, the photosensitive devices 50G, 50R, and 50B are silicon photodiodes. In addition, the photosensitive devices 50G, 50B, and 50R, the transmission transistor, and the charge storage 55 are integrated per pixel, and the photosensitive devices 50G, 50B, and 50R are included in the green pixel, the blue pixel, and the red pixel, respectively. The charge storage 55 is included in the near-infrared pixel.

The photosensitive elements 50G, 50B, and 50R sense green light, blue light, and red light, respectively, and the detected information is transmitted by a transmission transistor. In addition, the charge storage 55 is electrically connected to the photoelectric conversion device 100, and the information of the charge storage 55 is transmitted by the transmission transistor.

Metal wires and pads are provided on the semiconductor substrate 310, but the metal wires and pads may be provided under the photosensitive devices 50G, 50B, and 50R.

A lower insulation layer 60 is formed on the semiconductor substrate 310 on which metal wires and pads are formed.

The material constituting the lower insulation layer 60 may use the same material as the material constituting the insulation layer 80.

The color filter layer 70 is formed on the lower insulation layer 60.

The color filter layer 70 includes a blue filter 70B formed in a blue pixel, a green filter 70G formed in a green pixel, and a red filter 70R formed in a red pixel.

The upper insulation layer 80 is formed on the color filter layer 70 so as to planarize by removing steps by the color filter layer 70.

In the upper insulation layer 80 and the lower insulation layer 60, contact holes exposing the pads and through-holes 85 exposing the charge storage 55 are formed.

The photoelectric conversion device 100 is formed on the upper insulation layer 80.

The photoelectric conversion device 100 includes the first electrode 10, the photoelectric conversion film 30, and the second electrode 20 as described above. Herein, the first electrode 10 is a light-transmitting electrode capable of transmitting visible light. In addition, the second electrode 20 is a light-transmitting electrode capable of transmitting visible light and near-infrared light. Therefore, when light including near-infrared light and visible light is incident from the second electrode 20 side, near-infrared light is absorbed in the photoelectric conversion film 30 to be photo-electrically converted. On the other hand, the light that is not absorbed in the photoelectric conversion film 30, for example, visible light passes through the first electrode 10 and the color filter layer 70, and is detected by the photosensitive devices 50G, 50B, and 50R.

In addition, a band pass filter that transmits only visible light and near-infrared light may be installed in the upper surface of the photoelectric conversion device 100.

Figure 7:
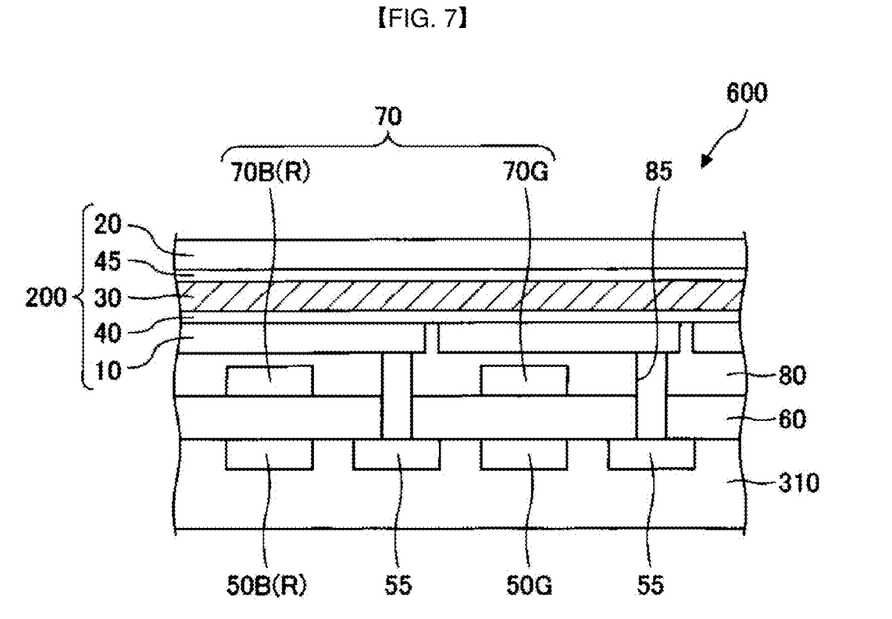
FIG. 7 is a schematic cross-sectional view showing a fourth example of an image sensor according to an embodiment.

FIG. 7 shows a fourth example of an image sensor according to an embodiment.

An image sensor 600 has the same configuration as the image sensor 500 except that the photoelectric conversion device 200 is applied instead of the photoelectric conversion device 100.

Figure 8:
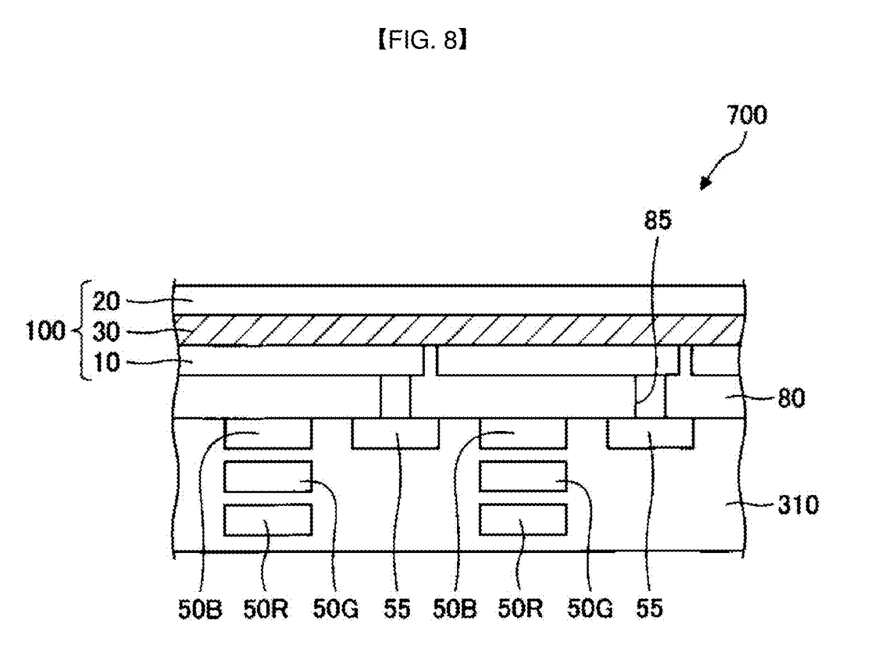
FIG. 8 is a schematic cross-sectional view showing a fifth example of an image sensor according to an embodiment.
Figure 9:
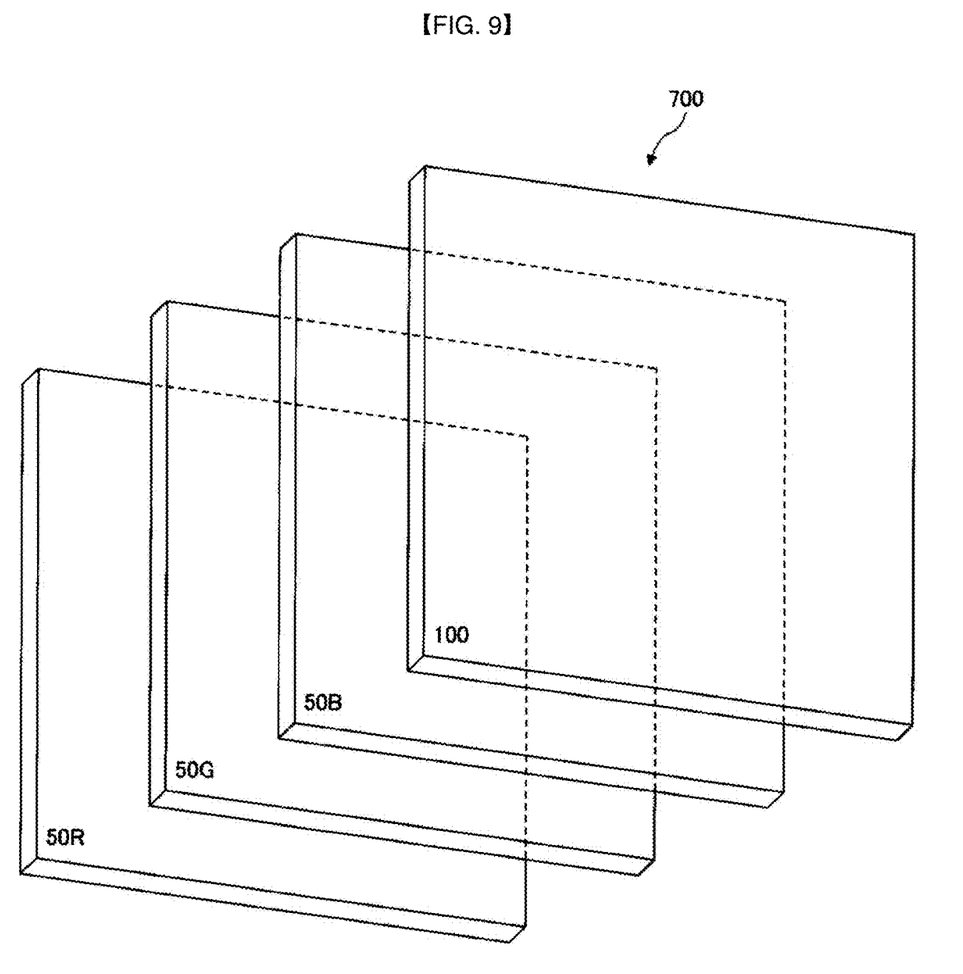
FIG. 9 is a schematic perspective view showing a fifth example of an image sensor according to an embodiment.

FIGS. 8 and 9 show a fifth example of an image sensor according to an embodiment.

An image sensor 700, like the image sensor 500, includes a semiconductor substrate 310, an insulation layer 80, and a photoelectric conversion device 100, and in the semiconductor substrate 310, photosensitive devices 50G, 50B, and 50R, a transmission transistor, a charge storage 55 are integrated.

However, unlike the image sensor 500, the image sensor 700 includes photosensitive devices 50B, 50G and 50R which are stacked, and the color filter layer 70 is omitted.

The photosensitive devices 50B, 50G and 50R are electrically connected to the charge storage, and the information of the charge storage is transmitted by the transmission transistor.

The photosensitive devices 50B, 50G and 50R may selectively absorb blue light, green light, and red light, respectively, depending on a stacking depth.

The image sensor 700 may be down-sized because the photoelectric conversion device 100 and the photosensitive devices 50B, 50G, and 50R are stacked.

Instead of the photosensitive devices 50G, 50B, and 50R, organic photoelectric conversion devices capable of selectively absorbing green light, blue light, and red light may be used. As a result, the sensitivity of the image sensor may be improved, and crosstalk may be reduced. In this case, the order of stacking the photoelectric conversion device 100 and the organic photoelectric conversion devices capable of selectively absorbing green light, blue light, and red light is not particularly limited.

In addition, instead of the photoelectric conversion device 100, the photoelectric conversion device 200 may be applied.

The image sensor according to an embodiment may be applied to various electronic devices, such as, a mobile phone, a digital camera, and the like.

EXAMPLES

Examples of an embodiment of the present disclosure are described. However, such examples are for illustration, and the technical ranges of the present disclosure are not limited to these examples.

Example 1: Preparation of p-Type Organic Semiconductor 1,3-Diiminobenz[f]isoindoline (2.0 g) (Tokyo Kasei, Inc.) and di-t-butyltin dichloride (1.5 g) (Sigma-Aldrich Co., Ltd.) are stirred in 1-chloronaphthalene under a reflux for 2 hours, and the reaction mixed solution is cooled down to room temperature. Then, precipitates are filtered therefrom, and then, washed with chloroform, pyridine, and methanol to obtain Compound 1 (1.5 g) as a p-type organic semiconductor.

Compound 1

Comparative Example 1

As for a p-type organic semiconductor, tin naphthalocyanine (Sigma-Aldrich Co., Ltd.) is used.

Evaluation 1: Heat Resistance Evaluation of P-Type Organic Semiconductor

Heat resistances of the p-type organic semiconductors of Example 1 and Comparative Example 1 are evaluated by measuring each temperature at which 2% and 5% weight losses occur by using thermogravimetry data (TG-DTA).

In Table 1, the heat resistance evaluation results are shown.

TABLE 1

| | Temperature at which 2% weight loss occurs [° C.] | Temperature at which 5% weight loss occurs [° C.] |
|---|---|---|
| Example 1 | 420 | >450 |
| Comparative Example 1 | 220 | 316 |

Referring to Table 1, the p-type organic semiconductor of Example 1 exhibits higher heat resistance than that of the p-type organic semiconductor of Comparative Example 1.

Without being bound by a specific theory, the reason is that as for the p-type organic semiconductor of Comparative Example 1 unlike the p-type organic semiconductor of Example 1, an axial substituent is not introduced into the tin naphthalocyanine.

Example 2: Manufacture of Photoelectric Conversion Device

An electron blocking layer is formed by thermally depositing Compound A represented by Chemical Formula A to be 20 nm thick on a glass substrate adhered with ITO (a film thickness: 150 nm).

Compound A

Subsequently, an photoelectric conversion film is formed to be 150 nm thick by depositing the p-type organic semiconductor of Example 1 and fullerene C60 as an n-type organic semiconductor in a volume ratio of 1:1 in a resistive heating deposition method. In addition, an ITO layer is formed to be 10 nm thick in a high frequency magnetron sputtering method, obtaining a photoelectric conversion device.

Herein, a vacuum degree in a vacuum process is set to be less than or equal to $4 \times 10^{-4}$ Pa.

Comparative Example 2: Manufacture of Photoelectric Conversion Device

A photoelectric conversion device of Comparative Example 2 is obtained according to the same method as Example 2 except that the p-type organic semiconductor of Comparative Example 1 is used instead of the p-type organic semiconductor of Example 1.

Evaluation 2: External Quantum Efficiency (IPCE) of Photoelectric Conversion Device The photoelectric conversion devices of Example 2 and Comparative Example 2 are sent into a glove box, without being exposed to the air, where each concentration of moisture and oxygen is maintained at less than or equal to 1 ppm, and the glove box is sealed with a glass sealing can having an adherent on by using a UV curing resin.

While a minus bias voltage of 3 V is respectively applied to the lower electrodes of the photoelectric conversion devices by using an IPCE-measuring system (Mcscience Inc.), external quantum efficiency (IPCE) at a maximum value of conversion efficiency in a wavelength range of 810 nm and 940 nm is measured.

IPCE evaluation results of the photoelectric conversion devices are shown in Table 2.

TABLE 2

|  | IPCE [%] | |
| --- | --- | --- |
|  | 810 nm | 940 nm |
| Example 2 | 24 | 13 |
| Comparative Example 2 | 9 | 4 |

Referring to Table 2, the photoelectric conversion device of Example 2 exhibits high IPCE anywhere in the wavelength range of 810 nm and 940 nm.

On the contrary, the photoelectric conversion device of Comparative Example 2, which includes the p-type organic semiconductor of Comparative Example 1, exhibits low IPCE. The reason is that the p-type organic semiconductor of Comparative Example 1 is thermally deteriorated when the photoelectric conversion film is formed in the resistive heating deposition method.

While this disclosure has been described in connection with what is presently considered to be practical example embodiments, it is to be understood that inventive concepts are not limited to the disclosed embodiments. On the contrary, inventive concepts are intended to cover various modifications and equivalent arrangements included within the spirit and scope of the appended claims.

DESCRIPTION OF SYMBOLS

10: first electrode
20: second electrode
30: photoelectric conversion film
100, 200: photoelectric conversion device
300, 400, 500, 600, 700: image sensor

What is claimed is:

1. A p-type organic semiconductor represented by Chemical Formula (1):

Chemical Formula (1)

wherein, in Chemical Formula (1), $R_1$ and $R_2$ are independently a substituted or unsubstituted C1 to C30 alkyl group, and $R_3$ to $R_{26}$ are independently a hydrogen atom, a deuterium atom, a substituted or unsubstituted alkyl group, a substituted or unsubstituted aryl group, a substituted or unsubstituted alkylthio group, a substituted or unsubstituted arylthio group, an oxy group substituted with a substituted or unsubstituted heterocyclic group, a thio group substituted with a substituted or unsubstituted heterocyclic group, or a substituted or unsubstituted amino group.

2. The p-type organic semiconductor of claim 1, wherein $R_1$ and $R_2$ of Chemical Formula (1) are independently a substituted or unsubstituted C3 to C20 branched alkyl group.

3. The p-type organic semiconductor of claim 1, wherein $R_3$ to $R_{26}$ of Chemical Formula (1) are independently a hydrogen atom, a deuterium atom, a substituted or unsubstituted C1 to C10 alkyl group, a substituted or unsubstituted C6 to C20 aryl group, a substituted or unsubstituted C1 to C10 alkylthio group, a substituted or unsubstituted C6 to C10 arylthio group, an oxy group substituted with a substituted or unsubstituted C4 to C10 heterocyclic group, a thio group substituted with a substituted or unsubstituted C4 to C10 heterocyclic group, or a substituted or unsubstituted C1 to C10 amino group.

4. The p-type organic semiconductor of claim 1, wherein $R_3$ to $R_{26}$ of Chemical Formula (1) are independently a hydrogen atom or a deuterium atom.

5. The p-type organic semiconductor of claim 1, wherein the p-type organic semiconductor represented by Chemical Formula (1) is represented by Chemical Formula (2):

Chemical Formula (2)

(2)

wherein, in Chemical Formula (2), $n_1$ and $n_2$ are independently an integer of 0 to 10, $Y_1$ to $Y_6$ are independently a C1 to C27 linear alkyl group, a sum of the $n_1$ value and a carbon number of $Y_1$ to $Y_3$ is 3 to 29, a sum of the $n_2$ value and a carbon number of $Y_4$ to $Y_6$ is 3 to 29, $R_3$ to $R_{26}$ are independently the same as defined in claim 1, and $R_{27}$ to $R_{30}$ are independently a hydrogen atom or a deuterium atom.

6. The p-type organic semiconductor of claim 5, wherein $R_3$ to $R_{26}$ are independently a hydrogen atom, a deuterium atom, a substituted or unsubstituted C1 to C10 alkyl group, a substituted or unsubstituted C6 to C20 aryl group, a substituted or unsubstituted C1 to C10 alkylthio group, a substituted or unsubstituted C6 to C10 arylthio group, an oxy group substituted with a substituted or unsubstituted C4 to C10 heterocyclic group, a thio group substituted with a substituted or unsubstituted C4 to C10 heterocyclic group, or a substituted or unsubstituted C1 to C10 amino group.

7. The p-type organic semiconductor of claim 5, wherein $R_3$ to $R_{26}$ are independently a hydrogen atom or a deuterium atom.

8. The p-type organic semiconductor of claim 5, wherein both of $n_1$ and $n_2$ are 0, and all of $Y_1$ to $Y_6$ are methyl groups.

9. The p-type organic semiconductor of claim 8, wherein $R_3$ to $R_{26}$ are independently a hydrogen atom or a deuterium atom.

10. A composition comprising:
the p-type organic semiconductor of claim 1, and
an n-type organic semiconductor.

11. The composition of claim 10, wherein the n-type organic semiconductor is fullerene, a derivative of fullerene, or a combination thereof.

12. A photoelectric conversion device comprising:
a first electrode,
a second electrode facing the first electrode, and
a photoelectric conversion film disposed between the first electrode and the second electrode,
wherein the photoelectric conversion film includes the p-type organic semiconductor of claim 1 and an n-type organic semiconductor.

13. The photoelectric conversion device of claim 12, further comprising:
an electron blocking layer between the first electrode and the photoelectric conversion film,
a hole blocking layer between the second electrode and the photoelectric conversion film, or
an electron blocking layer between the first electrode and the photoelectric conversion film and a hole blocking layer between the second electrode and the photoelectric conversion film.

14. An image sensor comprising:
the photoelectric conversion device of claim 12.

15. The image sensor of claim 14, further comprising:
one or more of a blue pixel, a green pixel, or a red pixel, wherein
the blue pixel, green pixel, and the red pixel include a blue photosensitive device, a green photosensitive device, and a red photosensitive device, respectively.

16. The image sensor of claim 15, wherein at least one of the blue photosensitive device, the green photosensitive device, and the red photosensitive device is a silicon photodiode.

17. The image sensor of claim 15, wherein at least one of the blue photosensitive device, the green photosensitive device, and the red photosensitive device is an organic photoelectric conversion device that is configured to selectively absorb one or more of blue light, green light, and red light.

18. The image sensor of claim 15, wherein
the image sensor includes at least two of the blue photosensitive device, the green photosensitive device, or the red photosensitive device,
wherein the at least two of the blue photosensitive device, the green photosensitive device, or the red photosensitive device are stacked.

* * * * *